United States Patent [19]

Renner

[11] Patent Number: 4,667,003
[45] Date of Patent: * May 19, 1987

[54] CROSSLINKED POLYMERS PREPARED FROM ALLYL OR METHALLYL-BICYCLO[2,2,1]HEPT-5-ENE-2,3-DICARBOXYLIC ACID IMIDES AND BISIMIDES

[75] Inventor: Alfred Renner, Muntelier, Switzerland

[73] Assignee: Ciba-Geigy Corporation, Ardsley, N.Y.

[*] Notice: The portion of the term of this patent subsequent to May 6, 2003 has been disclaimed.

[21] Appl. No.: 691,981

[22] Filed: Jan. 16, 1985

Related U.S. Application Data

[62] Division of Ser. No. 517,096, Jul. 25, 1983, Pat. No. 4,515,962.

[30] Foreign Application Priority Data

Aug. 5, 1982 [CH] Switzerland .................. 4715/82

[51] Int. Cl.⁴ .................. C08F 26/06; C08F 122/40
[52] U.S. Cl. .................. 526/259; 526/262; 526/280; 528/322
[58] Field of Search .................. 526/262, 280, 259; 528/322

[56] References Cited

U.S. PATENT DOCUMENTS

| | | | |
|---|---|---|---|
| 2,393,999 | 2/1946 | McCrone | 260/326 |
| 2,424,220 | 7/1947 | Bousquet | 167/24 |
| 3,105,839 | 10/1963 | Renner | 260/346.3 |
| 3,334,075 | 8/1967 | Kehn | 260/85.3 |
| 3,450,711 | 6/1969 | Megna et al. | 260/326 |
| 3,839,358 | 10/1974 | Bargain | 260/326.26 |
| 3,879,349 | 4/1975 | Bilow et al. | 260/47 UA |
| 4,229,351 | 10/1980 | Kiefer et al. | 260/326.26 |
| 4,271,074 | 6/1981 | Lohmann et al. | 260/326.26 |
| 4,380,643 | 4/1983 | Yoshida et al. | 548/260 |
| 4,526,962 | 5/1985 | Renner | 548/435 |
| 4,587,317 | 5/1986 | Renner | 526/262 |

FOREIGN PATENT DOCUMENTS 32745 7/1981 European Pat. Off. .
1277790 6/1972 United Kingdom .

OTHER PUBLICATIONS

A. K. St. Clair et al., Polym. Eng. Sci., 22, 9 (1982).

Primary Examiner—Harold D. Anderson
Attorney, Agent, or Firm—Luther A. R. Hall

[57] ABSTRACT

Crosslinked polymers with excellent physical properties are prepared by heating at 180°–300° C. the imides of the formula I

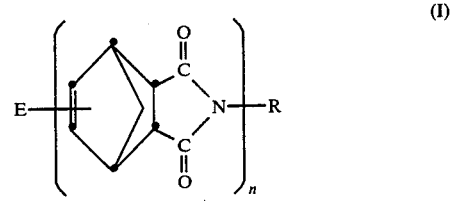

in which E is allyl or methallyl, R is hydrogen, alkyl, alkenyl, cycloalkyl, aryl or benzyl when n is 1, and R is alkylene or arylene when n is 2. The polymers can be used, in particular, for the preparation of glass fiber-reinforced and carbon fibre-reinforced plastics and as electrical insulating materials.

8 Claims, No Drawings

CROSSLINKED POLYMERS PREPARED FROM ALLYL OR METHALLYL-BICYCLO[2,2,1]HEPT-5-ENE-2,3-DICARBOXYLIC ACID IMIDES AND BISIMIDES

This is a divisional of application Ser. No. 517,096, filed July 25, 1983, now U.S. Pat. No. 4,515,962, issued on May 7, 1985.

The invention relates to bicyclo[2.2.1]hept-5-ene-2,3-dicarboxylic acid imides substituted by allyl or methallyl, their preparation and the polymers obtainable therefrom by heating.

Maleimides and bismaleimides, as well as N-allyl-monomaleimides are known.

U.S. Pat. No. 3,334,075 describes the curing of halogenated olefinic rubber polymers with selected polymaleimide compounds, such as N,N'-m-phenylene-bismaleimide. These polymaleimides contain no allyl or norbornenyl groups.

British Pat. No. 1,277,790 describes resin-forming compositions containing maleimide or bismaleimide derivatives, such as N-phenylmaleimide and methylene-bis-(N-phenylmaleimide). None of these compounds contains norbornenyl or allyl groups.

U.S. Pat. No. 3,839,358 describes a process for the preparation of bismaleimides by reacting a bismaleamic acid with the anhydride of a low molecular weight carboxylic acid in the presence of a tertiary amine, an organic solvent and a nickel catalyst. U.S. Pat. No. 4,229,351 describes a process for the preparation of mono- and bis-maleimides containing aliphatic substituents on the nitrogen atom. The preparation of compounds with allyl-substituted norbornenyl groups is neither described nor suggested in either one or the other patent.

U.S. Pat. No. 3,450,711 relates to bisimide compounds which are prepared by reacting endo,cis-bicyclo[2.2.1]hept-5-ene-2,3-dicarboxylic acid anhydride (=5-norbornene-2,3-dicarboxylic acid anhydride) with selected organic diamines. These bisimides contain no allyl substituents and differ from the present compounds both in respect of their structure and in respect of their chemical reactivity. The compounds according to this U.S. patent are used as intermediates in the preparation of epoxide compounds.

It is also known that polyimide oligomers can be prepared by an addition reaction between 3,3',4,4'-benzophenonetetracarboxylic acid dianhydride and diaminodiphenylmethane in the presence of various compounds capable of crosslinking and masking end groups, such as unsubstituted or chlorinated 5-norbornenecarboxylic acid anhydride and 5-vinylphthalic acid anhydride, these oligomers being used as adhesives [cf., for example, Polym, Eng. Sci., 22, 9-14 (1982)]. These polyimide oligomers contain no allyl groups.

U.S. Pat. No. 4,271,074 describes silanes prepared from imide intermediates, for example N-allyl-2,3-dimethylmaleimide. The monomers according to the invention have a norbornenyl group substituted by an allyl group, and are therefore structurally quite different and are not suggested by this patent.

The preparation of the starting substances for the compounds according to the invention is described in U.S. Pat. No. 3,105,839.

The allyl- or methallyl-substituted bicyclo[2.2.1]-hept-5-ene-2,3-dicarboxylic acid imides according to the invention are useful starting substances for polymers of excellent properties. They have the following formula I:

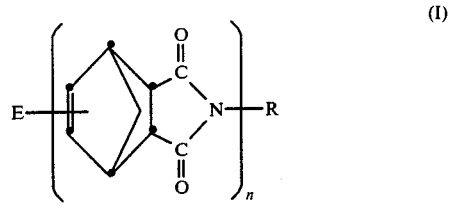

in which E is allyl or methallyl, n is 1 or 2 and, if n is 1, R is hydrogen, alkyl having 1-12 C atoms, alkenyl having 3-6 C atoms, cycloalkyl having 5-8 C atoms, aryl having 6-10 C atoms or benzyl or, if n is 2, R is $-C_mH_{2m}-$, in which m=2-20, arylene having 6-10 C atoms or a group of the formula II

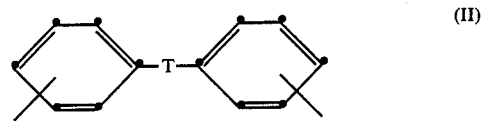

in which T is methylene, isopropylidene, CO, O, S or $SO_2$.

E is preferably the allyl group.

R can be a straight-chain or branched alkyl group having 1-12 C atoms, such as methyl, ethyl, isopropyl, n-butyl, isopentyl, n-hexyl, 2-ethyl-hexyl, n-decyl or n-dodecyl, and is preferably alkyl having 1-8 C atoms.

R can also be a straight-chain or branched alkenyl group having 3-6 C atoms, such as allyl, methallyl, 2-butenyl and 3-hexenyl, preferably allyl.

A cycloalkyl group R can be a cyclopentyl, cyclohexyl, cycloheptyl or cyclooctyl group, preferably cyclohexyl.

An aryl group R can be unsubstituted phenyl or a phenyl group which is substituted by one or two methyl groups, such as tolyl or xylyl, or naphthyl. The phenyl group is preferred. A $-C_mH_{2m}-$ group R can be a straight-chain or branched radical, such as ethylene, propylene, trimethylene, tetramethylene, hexamethylene, octamethylene or dodecamethylene. A group R of the formula II is preferably bonded to the N atoms in the 4,4'-positions.

R is preferably a $-(CH_2)_m-$ group, in which m=2 to 12.

An arylene group R having 6-10 C atoms is, for example, a m-phenylene, p-phenylene, 1,3-naphthylene, 1,4-naphthylene or 1,5-naphthylene group.

In a group R of the formula II, T is preferably the methylene group, O or $SO_2$.

Preferred compounds of the formula I are those in which E is allyl and, if n is 1, R is hydrogen, alkyl having 1-8 C atoms, allyl, cyclohexyl, phenyl or benzyl, or, if n is 2, R is $-(CH_2)_m-$, in which m=2-12, m- or p-phenylene or a group of the formula II, in which T is the methylene group, O or $SO_2$.

Particularly preferred compounds of the formula I are those in which E is the allyl group, n is the number 2 and R is $-(CH_2)_2-$, $-(CH_2)_6-$ or

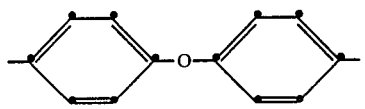

or, in particular,

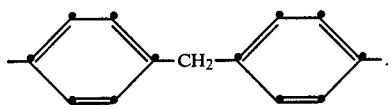

The imides according to the invention can be prepared in a manner which is known per se, for example by reacting an anhydride of the formula III

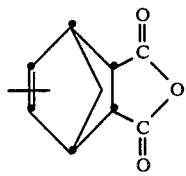 (III)

with a compound of the formula IV

  (IV)

$(H_2N)_{\overline{n}}R$ in which E, R and n are as defined under formula I, at elevated temperature, the water formed during the reaction being distilled off. If the compounds of the formula IV are ammonia or a low-boiling monoamine, an excess of these reactants is recommended. Diamines are advantageously to be used in a stoichiometric ratio. The reaction can be carried out without a solvent or in the presence of an inert solvent, which can be used for azeotropic removal of the water (entrainer). The temperature of the reaction can be between 100° and 250° C. The imides of the formula I are preferably prepared in the melt under a pressure of at most 4,500 Pa at temperatures between 130° and 220° C., in particular 180° and 220° C.

As already mentioned, the starting substances of the formula III can be prepared by the process described in U.S. Pat. No. 3,105,839 by reaction of sodium cyclopentadienide with an allyl or methallyl halide, followed by a Diels-Alder reaction with maleic anhydride. Although the U.S. patent specification states that the allyl group is bonded in the 7-position of the bicyclic system, more recent investigations show that an isomer mixture in respect of the position of the allyl group and also in respect of the endo- and exo-configuration of the anhydride moiety is formed. It has not yet been possible to isolate the isomeric components by conventional methods of separation.

The monoamines or diamines used of the formula IV are known, or they can be prepared by processes which are known per se.

The compounds according to the invention are liquid or low-melting solid substances which can be polymerised to solid products with a high glass transition temperature and stability to heat and water. These products can be used in many ways, for example as casting resins or adhesives, and in particular for the production of glass fiber-reinforced or carbon fiber-reinforced plastics, and as electrical insulating materials.

The compounds according to the invention can be used and polymerised directly, or they can first be dissolved in an organic solvent, such as toluene, xylene, methyl ethyl, ketone, an ethylene glycol monoalkyl or dialkyl ether having 1–4 C atoms in the alkyl groups or a similar solvent conventional in the coatings industry. Such solutions can be used as impregnating agents or coating agents, or they can be dispatched to the consumer.

The invention also relates to the novel polymers which can be obtained by heating an imide of the formula I at a temperature between 180° and 300° C., preferably between 200° and 250° C., for 6 to 24 hours. The above statements apply in respect of preferred definitions of E, R and n, Particularly preferred polymers are those which can be obtained by heating an imide of the formula I in which E is the allyl group, n is the number 2 and R is the group

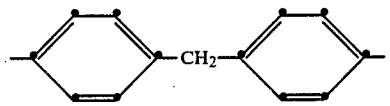

at 240° to 250° C. for 6–12 hours. No catalysts which substantially accelerate the polymerisation have yet been found.

Inert and stable substances, such as fillers, pigments, dyes and other additives, can, of course, be added to the imides of the formula I before they are polymerised to crosslinked structures.

EXAMPLE 1

Preparation of allyl-bicyclo[2.2.1]hept-5-ene-2,3-dicarboxylic acid imide.

A mixture of 102 g of allyl-bicyclo[2.2.1]-hept-5-ene-2,3-dicarboxylic acid anhydride, prepared according to Example 1 in U.S. Pat. No. 3,105,839, and 68.1 g of 25% aqueous ammonia solution is refluxed with cooling at 95°–102° C. for 70 minutes, while stirring. The water and excess ammonia are then distilled off under reduced pressure (6,133 Pa). When the internal temperature reaches 120° C., 54 ml of aqueous ammonia have been distilled off. An orange-coloured, viscous residue remains, and is distilled under a pressure of 13.3 Pa. 62.07 g of allyl-bicyclo[2.2.1]-hept-5-ene-2,3-dicarboxylic acid imide pass over between 132° and 135° C., corresponding to a yield of 60% of theory. The imide is a yellow oil of refractive index $n_D^{20}$ 1.5421 and viscosity $\eta_{25}$ 345 Pa.s at 25° C.

| Analysis | % C | % H | % N |
|---|---|---|---|
| calculated for $C_{12}H_{13}NO_2$: | 70.9 | 6.45 | 6.90 |
| found: | 70.7 | 6.6 | 6.9 |

IR spectrum: 1,620 cm$^{-1}$ cyclic double bond; 1,640 cm$^{-1}$ allyl group; 1,725 cm$^{-1}$ carbonyl group; 1,772 cm$^{-1}$ carbonyl in the cyclic imide; and 3,390 cm$^{-1}$ NH vibration.

After polymerisation at 240° C. for 24 hours, a solid substance with a glass transition temperature of 218.5° C. is obtained. It no longer has the IR absorption frequencies at 1,620 and 1,640 cm$^{-1}$ characteristics of double bonds.

EXAMPLE 2

Allyl-bicyclo[2.2.1]hept-5-ene-2,3-dicarboxylic acid N-methylimide.

A mixture of 204 g of the anhydride used in Example 1 and 113 g of a 33 percent by weight solution of methylamine in alcohol is refluxed with cooling at 65° C., while stirring. An exothermic reaction occurs at this temperature. The mixture is cooled somewhat and warmed at 60°–65° C. for a further 2.5 hours and the alcohol, excess methylamine and a little water are distilled off (111 ml). When the internal temperature reaches 165° C., the pressure is reduced in steps to 6,665 Pa and the mixture is kept under these conditions for 30 minutes.

Distillation of the red-brown crude product gives, at 104°–110° C. under 12 Pa, 165.62 g (76% of theory) of a yellow oil of $n_D^{20}$ 1.5269 and $\eta_{25}$ =1 Pa.s.

| Analysis: | % C. | % H | % N |
|---|---|---|---|
| calculated for $C_{13}H_{15}NO_2$: | 71.87 | 6.96 | 6.45 |
| found: | 72 | 7.0 | 6.6 |

Polymerisation at 240° C. for 24 hours gives a solid substance which has a glass transition temperature (GTT) of 218.5° C. and shows no C=C absorption frequency at 1,620 and 1,640 cm$^{-1}$ in the IR spectrum.

EXAMPLE 3

Allyl-bicyclo[2.2.1]hept-5-ene-2,3-dicarboxylic acid N-allylimide.

377.6 g of allyl-bicyclo[2.2.1]hept-5-ene-2,3-dicarboxylic acid anhydride are mixed with 131.9 g of allylamine and the mixture is heated, using a descending condenser, until the internal temperature reaches 175° C. 59 ml of distillate (water and excess allylamine) are obtained. On distillation, 399.32 g (88.7% of theory) of a light yellow oil of $n_D^{20}$ 1.5272 and $\eta_{25}$ 0.69 Pa.s are obtained at between 120° and 123° C. under 40 Pa.

| Analysis: | % C | % H | % N |
|---|---|---|---|
| calculated for $C_{15}H_{17}NO_2$: | 74.05 | 7.05 | 5.76 |
| found: | 74.2 | 7.1 | 5.8 |

Polymerisation at 240° C. for 24 hours gives a solid substance with a GTT >290° C. No C=C absorption frequencies can be detected at 1,620 and 1,640 cm$^{-1}$ in the IR spectrum.

EXAMPLE 4

Allyl-bicyclo[2.2.1]hept-5-ene-2,3-dicarboxylic acid N-(2-ethyl-hexyl)-imide.

The procedure described in Example 3 is repeated, except that 204 g of allyl-bicyclo[2.2.1]hept-5-ene-2,3-dicarboxylic acid anhydride and 129 g of 2-ethylhexylamine are used. 17 g of water are split off ayt 115° to 160° C. under 4,000 Pa in the course of 4.5 hours. 292.05 g (92.6% of theory) of a fraction of boiling point 160°–164° C. under 10.7 Pa, $n_D^{20}$ 1.5038 and $\eta_{25}$ 0.68 Pa.s are obtained.

| Analysis | % C | % H | % N |
|---|---|---|---|
| calculated for $C_{20}H_{29}NO_2$: | 76.15 | 9.27 | 4.44 |
| found: | 76.2 | 9.4 | 4.4 |

EXAMPLE 5

Allyl-bicyclo[2.2.1]hept-5-ene-2,3-dicarboxylic acid N-cyclohexylimide.

102 g of allyl-bicyclo[2.2.1]hept-5-ene-2,3-dicarboxylic acid anhydride and 100 g of cyclohexylamine are heated to 137° C. under 4,000 Pa. 59 ml of water and excess cyclohexylamine are distilled off. Distillation of the residue at 162°–163° C. under 10.7 Pa gives 87.6 g (62% of theory) of an oil of $n_D^{20}$ 1.5296 and $\eta_{25}$ 72.8 Pa.s.

| Analysis: | % C | % H | % N |
|---|---|---|---|
| calculated for $C_{18}H_{23}NO_2$: | 75.8 | 8.07 | 4.91 |
| found: | 75.5 | 7.95 | 4.95 |

EXAMPLE 6

Allyl-bicyclo[2.2.1]hept-5-ene-2,3-dicarboxylic acid N-phenylimide.

93 g of aniline are added dropwise to 102 g of allyl-bicyclo[2.2.1]hept-5-ene-2,3-dicarboxylic acid anhydride, while stirring. During this addition, the temperature rises to 80° C. The mixture is heated to 150° C. and the pressure is reduced to 4,266 Pa. 9 ml of water and 46 ml of aniline distil off. Distillation gives 82.37 g (60% of theory) of a viscous yellow oil of boiling point 183° C. under 12 Pa, $n_D^{20}$ 1.5738 and $\eta_{25}$ 105.6 Pa.s.

| Analysis: | % C | % H | % N |
|---|---|---|---|
| calculated for $C_{18}H_{17}NO_2$: | 77.4 | 6.14 | 5.02 |
| found: | 77.2 | 6.4 | 5.02 |

Polymerisation at 240° C. for 24 hours gives a solid substance with a GTT of 230° C. No absorption frequencies for

are found in the IR spectrum (1,620 and 1,640 cm$^{-1}$).

EXAMPLE 7

Allyl-bicyclo[2.2.1]hept-5-ene-2,3-dicarboxylic acid N-benzylimide.

102 g of allyl-bicyclo[2.2.1]hept-5-ene-2,3-dicarboxylic acid anhydride and 85.6 g of benzylamine are boiled under reflux for 2 hours. Water and excess benzylamine are then distilled off (39 ml at 105° C. under 4,132 Pa).

Distillation at a boiling point of 170°–184° C. under 10.7 Pa gives 117.35 g (80% of theory) of a yellow oil of $n_D^{20}$ 1.5612 and $\eta_{25}$ 17.3 Pa.s.

| Analysis | % C | % H | % N |
|---|---|---|---|
| calculated for $C_{19}H_{19}NO_2$: | 77.79 | 6.53 | 4.87 |

| Analysis: | % C | % H | % N |
|---|---|---|---|
| found: | 77.5 | 6.7 | 5.1 |

EXAMPLE 8

N,N'-Ethylene-bis-(allyl-bicyclo[2.2.1]hept-5-ene-2,3-dicarboxylic acid imide).

204 g of allyl-bicyclo[2.2.1]hept-5-ene-2,3-dicarboxylic acid anhydride are taken and 30 g of ethylenediamine are added dropwise, while stirring. The temperature rises to 130° C. The temperature is increased to 180° C.; during this procedure, 14 ml of water distil off. The mixture is then heated at 200° C. under a pressure of 9.3 Pa for a further 2 hours. 210 g of a yellow resin which is solid at room temperature and has a softening point of 56° C., measured on a Kofler hot bench, are obtained.

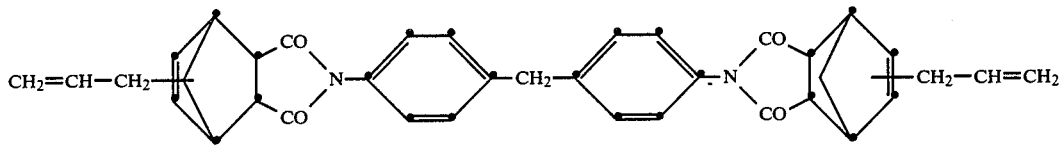

Molecular weight (number-average) $\overline{M}_n=504$, (weight-average) $\overline{M}_w=1,204$, determined by the gel permeation chromatography method.

| Analysis: | % C | % H | % N |
|---|---|---|---|
| calculated for $C_{26}H_{28}N_2O_4$: | 72.20 | 6.53 | 6.48 |
| found: | 71.7 | 6.5 | 6.4 |

After polymerisation at 240° C. for 12 hours, a solid substance with a glass transition temperature of 354° C. is obtained.

EXAMPLE 9

N,N'-Hexamethylene-bis-(allyl-bicyclo[2.2.1]hept-5-ene-2,3-dicarboxylic acid imide).

A mixture of 204 g of allyl-bicyclo[2.2.1]hept-5-ene-2,3-dicarboxylic acid anhydride and 58 g of hexamethylenediamine is heated, over the course of 3 hours, to 175° C., with a descending condenser, while stirring. The pressure is then reduced to 1,866 Pa and the mixture is stirred at 175° C. for a further hour. 235 g of an amber-coloured resin which is just still liquid at room temperature are obtained.

| Analysis: | % C | % H | % N | |
|---|---|---|---|---|
| calculated for $C_{30}H_{36}N_2O_4$: | 73.74 | 7.43 | 5.73 | $\overline{M}_n = 560$ |
| found: | 73.4 | 7.4 | 5.5 | $\overline{M}_w = 1,173$ |

EXAMPLE 10

N,N'-Dodecamethylene-bis-(allyl-bicyclo[2.2.1]hept-5-ene-2,3-dicarboxylic acid imide).

100.66 g of allyl-bicyclo[2.2.1]hept-5-ene-2,3-dicarboxylic acid anhydride and 49.34 g of 1,12-diaminododecane are heated gradually at 200° C., finally in vacuo. 140 g of a viscous, amber-coloured resin are obtained.

| Analysis: | % C | % H | % N |
|---|---|---|---|
| calculated for $C_{36}H_{50}O_4N_2$: | 75.22 | 8.77 | 4.87 |
| found: | 75.8 | 8.75 | 5.1 |

EXAMPLE 11

Bis-[4-(Allyl-bicyclo[2.2.1]hept-5-ene-2,3-dicarboximidophenyl)-methane].

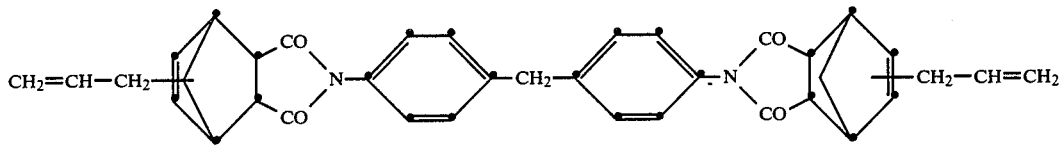

204 g of allyl-bicyclo[2.2.1]hept-5-ene-2,3-dicarboxylic acid anhydride and 99 g of 4,4'-diaminodiphenylmethane are heated to 200° C. in vacuo and kept under these conditions for 1 hour. 280 g of a brown solid resin with a softening point of 104° C., a viscosity of 0.425 Pa.s at 200° C. and an acid number of 0 are obtained.

| Analysis: | % C | % H | % N | |
|---|---|---|---|---|
| calculated for $C_{37}H_{34}N_2O_4$: | 77.87 | 6.01 | 4.91 | $\overline{M}_n = 977$ |
| found: | 78.2 | 6.1 | 5.0 | $\overline{M}_w = 4,718$ |

EXAMPLE 12

218 g of methallyl-bicyclo[2.2.1]hept-5-ene-2,3-dicarboxylic acid anhydride (boiling point=139°–142° C. under 20 Pa) and 99 g of 4,4'-diaminodiphenylmethane are heated to 200° C. in vacuo and kept at this temperature for 1 hour. 295 g of a brown solid resin with a softening point of 98° C. and an acid number of 2 mg of KOH/g are obtained.

| Analysis: | % C | % H | % N |
|---|---|---|---|
| calculated for $C_{38}H_{36}N_2O_4$: | 78.04 | 6.12 | 4.79 |
| found: | 78.3 | 6.1 | 4.8 |

EXAMPLE 13

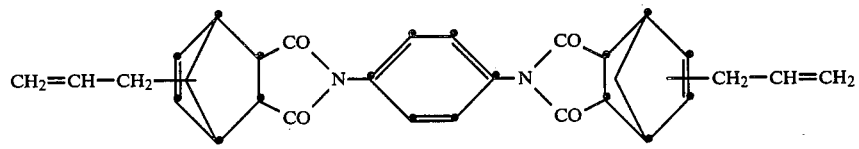

204 g of allyl-bicyclo[2.2.1]-hept-5-ene-2,3-dicarboxylic acid anhydride and 54.0 g of 1,4-phenylenediamine are heated at 220° C. under 2,000 Pa, the water of reaction being distilled off. 228 g (95% of theory) of a dark brown solid resin with a softening point of 140° C. are obtained.

| Analysis: | % C | % H | % N |
|---|---|---|---|
| calculated for $C_{30}H_{28}N_2O_4$: | 74.98 | 5.87 | 5.83 |
| found: | 74.7 | 6.1 | 6.1 |

EXAMPLE 14

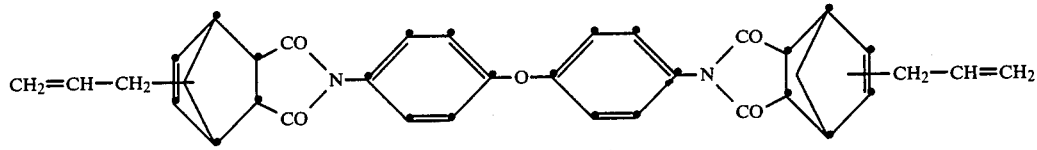

408 g of allyl-bicyclo[2.2.1]hept-5-ene-2,3-dicarboxylic acid anhydride and 204.3 g of 4,4'-diaminodiphenyl ether (melting point=188°-190° C., decomposition, 98% pure) are heated to 200° C. 35 cm³ of water thereby distil off. The pressure is reduced to 40 Pa, the mixture is heated to 220° C. and this temperature is maintained for one hour. 555.8 g of a dark brown solid resin (96.5% of theory) with a softening point of 142° C. are obtained.

| Analysis: | % C | % H | % N |
|---|---|---|---|
| calculated for $C_{36}H_{32}N_2O_5$: | 75.51 | 5.63 | 4.89% |
| found: | 75.5 | 5.7 | 4.9 |

EXAMPLE 15

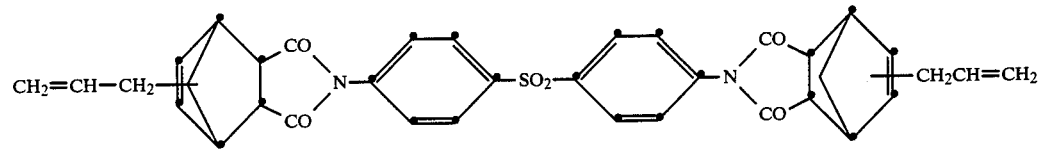

102 g of allyl-bicyclo[2.2.1]hept-5-ene-2,3-dicarboxylic acid anhydride and 62 g of 4,4'-diaminodiphenyl sulfone (melting point=174°-176° C.) are heated to 180° C., the pressure is reduced to 27 Pa and the mixture is kept under these conditions for 1 hour. 135.6 g of a brown solid resin (87.5% of theory) with a softening point of 108° C. are obtained.

PREPARATION OF CROSSLINKED POLYMERS

The compounds according to the invention have two or more olefinic double bonds in the molecule which are capable of polymerisation. On heating, crosslinked polymers with useful physical properties are obtained.

USE EXAMPLES

EXAMPLE I

The resin prepared according to Example 8 is poured as a mobile melt into a 12×12×0.4 cm³ steel mould pre-heated to 200° C. and is cured at 200° C. for 12 hours and at 240° C. for 12 hours. After cooling, the sheet is cut into test bars. The following properties are determined on these bars:

| Flexural strength acording to DIN 53,452: | 95.4 N/mm² |
|---|---|
| Flexural impact strength according to DIN 53,455: | 7.54 kJ/m² |
| Absorption of water in 1 hour at 100° C.: | 0.25% by weight |
| Vicat softening point according to DIN 53,460: | >250° C. |
| Weight loss after 30 days at 250° C. in air: | 2.23% by weight |

Sticking of metal: Anticorodal B metal strips (170×25 mm²) are stuck, with an overlap of 12.5 mm, with the resin melt from Example 8 and the melt is cured as described above. The tensile strength according to DIN 53,283 is 5.7 N/mm².

EXAMPLE II

The imide prepared according to Example 9 is poured as a hot, mobile resin into a 12×12×0.4 cm³ steel mould and is cured at 200° C. for 1 hour, at 220° C. for 1 hour and at 240° C. for 12 hours. After cooling, test bars are cut out of the sheet. The following properties are measured on these bars:

| Flexural strength according to DIN 53,452: | 89.8 N/mm² |
|---|---|
| Deflection: | 4.3 mm |
| Flexural impact strength according to DIN 53,455: | 9.2 kJ/m² |
| Vicat softening point according to DIN 53,460: | 247° C. |
| Absorption of water (1 hour at 100° C.): | 0.42% by weight |
| Tensile strength on Anticorodal according to DIN 53,283: | 7.2 N/mm² |

EXAMPLE III

The imide prepared according to Example 10 is poured into a 12×12×0.4 cm³ steel mould and is cured at 220° C. for 15 hours and at 240° C. for 4 hours. Test bars from the resulting sheet have the following properties:

| Flexural strength: | 89.7 N/mm² |
|---|---|
| Deflection: | 6.1 mm |
| Impact strength: | 14.4 kJ/m² |
| Vicat softening point: | 152° C. |
| Absorption of water (1 hour at 100° C.): | 0.43% by weight |

When sheet aluminium is stuck under the same hardening conditions, the two sheets to be stuck overlapping by 25×12 mm², an excellent tensile strength of 10±0.5 N/mm² is obtained according to DIN 53,283.

EXAMPLE IV

The casting resin prepared according to Example 11 is poured into a $12\times12\times0.4$ cm$^3$ steel mould and is cured at 220° C. for 6 hours and at 240° C. for 14 hours. Test bars have the following properties:

| | |
|---|---|
| Flexural strength: | 103.1 N/mm$^2$ |
| Deflection: | 2.3 mm |
| Impact strength: | 12.5 kJ/m$^2$ |
| Vicat softening point: | >260° C. |
| Absorption of water (1 hour at 100° C.): | 0.27% by weight |
| Tensile strength on Anticorodal according to DIN 53,283: | 5.3 N/mm$^2$ |

Stability To Heat

Thermal analysis in air at a heating rate of 2° C./minute:
  Start of decomposition at 390° C., 10% weight loss at 420° C.
Weight loss after 30 days at 250° C.: 2.4% by weight
Weight loss after 30 days at 275° C.: 3.8% by weight
Flexural strength after 30 days at 250° C.: 104.9 N/m$^2$
Flexural strength after 30 days at 275° C.: 68.5 N/mm$^2$

DIELECTRIC PROPERTIES

Dielectric constant $\epsilon$ at 22° C.: 3.3
Dielectric constant $\epsilon$ at 250° C.: 2.9
Dielectric loss factor according to DIN 53,483 at 22° C.: 0.16%
Dieletric loss factor according to DIN 53,483 at 250° C.: 0.42%
Specific volume resistivity according to DIN 53,482 at 22° C.: $2.8\times10^{16}$ ohm.cm
Specific volume resistivity according to DIN 53,482 at 250° C.: $1.3\times10^{13}$ ohm.cm.

EXAMPLE V

The imide resin prepared according to Example 14 is cast and cured as described in the preceding example. Test bars have the following properties:

| | |
|---|---|
| Flexural strength: | 99.3 N/mm$^2$ |
| Deflection: | 3.1 mm |
| Flexural impact strength: | 12.9 kj/m$^2$ |
| Vicat softening point: | >260° C. |
| Weight loss after 30 days at 275° C.: | 3.89% by weight |
| Absorption of water (1 hour at 100° C.): | 0.55% by weight |
| Tensile strength on Anticorodal according to DIN 53,283: | 6.2 N/mm$^2$ |

What is claimed is:

1. A polymer, which is obtained by heating an imide of formula I

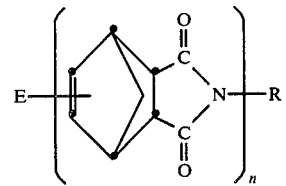

in which E is allyl or methallyl, n is 1 or 2 and, when n is 1, R is hydrogen, alkyl having 1–12 C atoms, alkenyl having 3–6 atoms, cycloalkyl having 5–8 C atoms, phenyl, tolyl, xylyl or naphthyl, or benzyl or, when n is 2, R is —C$_m$H$_{2m}$—, in which m is an integer of 2–20, m-phenylene, p-phenylene, 1,3-naphthylene, 1,4-naphthylene or 1,5-naphthylene or a group of the formula II

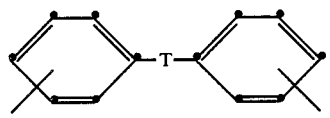

in which T is methylene, isopropylidene, CO, O, S or SO$_2$, at a temperature between 180° and 300° C. for 6 to 24 hours.

2. A polymer according to claim 1 where in the imide of formula I E is allyl.

3. A polymer according to claim 1 where in the imide of formula I
   E is the allyl group and, when n is 1, R is hydrogen, alkyl having 1–8 C atoms, allyl, cyclohexyl, phenyl or benzyl, or, when n is 2, R is —(CH$_2$)$_m$—, in which m is an integer of 2–12, m- or p-phenylene or a group of the formula II

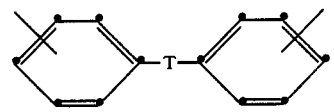

in which T is the methylene group, O or SO$_2$.

4. A polymer according to claim 1 where in the imide of formula I
   E is the allyl group, n is the number 2 and R is —(CH$_2$)$_2$—, —(CH$_2$)$_6$— or

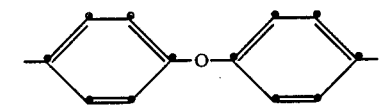

5. A polymer according to claim 1 where the imide of formula I is

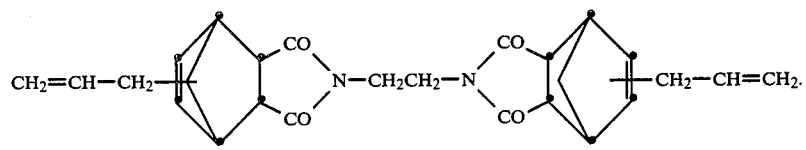

6. A polymer according to claim 1 where the imide of formula I is

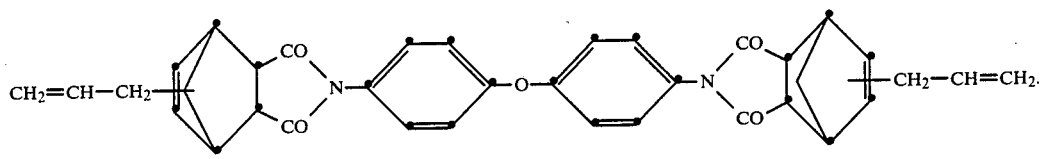
7. A polymer according to claim 1 where the imide of formula I is
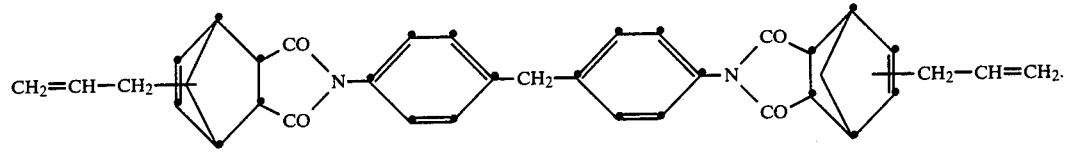
8. A polymer according to claim 1 which is obtained by heating an imide of formula I where E is allyl, n is 2 and R is
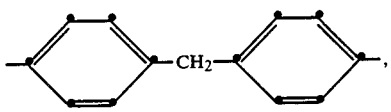
at a temperature of 240° to 250° C. for 6 to 12 hours.
* * * * *